United States Patent [19]

Pao

[11] Patent Number: 4,674,499
[45] Date of Patent: Jun. 23, 1987

[54] COAXIAL BIPOLAR PROBE

[76] Inventor: David S. C. Pao, 95 High Point Dr., Churchville, Pa. 18966

[21] Appl. No.: 690,266

[22] Filed: Jan. 10, 1985

Related U.S. Application Data

[60] Continuation-in-part of Ser. No. 611,867, May 18, 1984, abandoned, which is a division of Ser. No. 428,849, Sep. 30, 1982, Pat. No. 4,476,862, which is a division of Ser. No. 213,861, Dec. 8, 1980, abandoned, which is a continuation of Ser. No. 900,422, Feb. 5, 1979, abandoned.

[51] Int. Cl.$^4$ .............................................. A61B 17/39
[52] U.S. Cl. .......................... 128/303.14; 128/303.17
[58] Field of Search .................... 128/303.13–303.19; 604/21, 35

[56] References Cited

U.S. PATENT DOCUMENTS

| | | | |
|---|---|---|---|
| 1,814,791 | 7/1931 | Ende | 128/303.17 |
| 1,983,669 | 12/1934 | Kimble | 128/303.17 |
| 2,275,167 | 3/1942 | Bierman | 128/303.17 |
| 3,651,812 | 3/1972 | Samuels | 128/303.18 |
| 3,920,021 | 11/1975 | Hiltebrandt | 128/303.17 |
| 3,974,833 | 8/1976 | Durden | 128/303.17 X |
| 3,987,795 | 10/1976 | Morrison | 128/303.14 |
| 4,034,762 | 7/1977 | Cosens et al. | 128/303.17 |
| 4,103,688 | 8/1978 | Edwards | 128/303.17 |
| 4,301,802 | 11/1981 | Poler | 128/303.14 |
| 4,483,338 | 11/1984 | Bloom et al. | 128/303.13 |
| 4,548,207 | 10/1985 | Reimels | 128/303.17 |

FOREIGN PATENT DOCUMENTS 2101893  1/1983  United Kingdom .......... 128/303.13

OTHER PUBLICATIONS

Bipolar Forceps for Electrocautery Tonsillectomy, Reed et al., Transactions of AAOO, vol. 78, 1974.
Bipolar Coagulation in Ophthalmic Operations, McPherson, Jr., American Journal of Ophthamology, vol. 73, No. 5, May 1972.
Decker et al., "An Electrocautery Instrument . . . ", 10th Annual Rocky Mountain Bio. Eng. Symposium, Boulder, CO, May 7–9, 1973.
Schmidt et al., "Vas Cautery . . .", Urology, vol. III, No. 5, May 1974, pp. 604–605.
Pao, "Coaxial Bipolar Probe" Arch. Ophthalmol, vol. 97, 1351–1352, Jul. 1979.
"Spot Electrocautery with Coaxial Bipolar Probe" *Ophthalmology Times,* Jul. 1978.
Dr. Drew, Wet-Field Cautery Tip Works Like Pencil Eraser, IOL Occular Surgery News, Oct. 15, 1983 edition.
Peyman et al., "Experimental Intraocular Coagulator", Opthalmic Surgery, Jan.–Feb. 1972, vol. 3, No. 1.

*Primary Examiner*—Lee S. Cohen
*Attorney, Agent, or Firm*—Woodcock, Washburn, Kurtz, Mackiewicz & Norris

[57] ABSTRACT

Improves bipolar electrode probe devices for use in electrocautery and electrocoagulation include a central electrode having an outer electrode coaxially disposed therearound. The central and outer electrodes are electrically insulated from each other and are adapted to receive a high frequency voltage or direct voltage thereacross. The diameter of the central electrode as well as the inner and outer diameters of the outer electrode are dimensioned in accordance with the designated use of the probe, for example: general surgery, specialty surgery or microsurgery. In one of the improved embodiments, the central or axial electrode has an elongate untapered cylindrical shape having an exposed flat transverse surface at one end thereof. The outer electrode has an elongate hollow tubular shape which is coaxially disposed around the central electrode. A first end of the outer electrode is disposed behind the tip of the central electrode in order to form a probe end wherein the central electrode protrudes slightly beyond the plane defining the terminus of the outer electrode forming a tiered electrode structure. Depending upon the use, the probe end may be either straight or curved. Another embodiment includes a lumen through the center of the axial electrode. The electrodes are incorporated into an insulated holder which includes an electrical connector for mating to a high frequency voltage source when the lumen connector is provided and a fluidic connector for coupling the lumen with a source of irrigation, air or vacuum, or any of the three in alternation, as desired.

16 Claims, 19 Drawing Figures

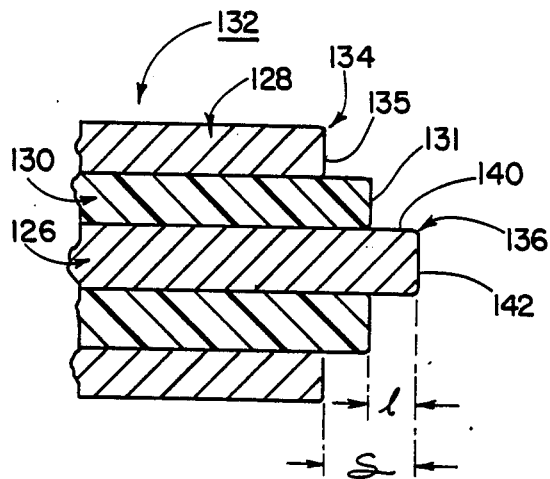
FIG. 6
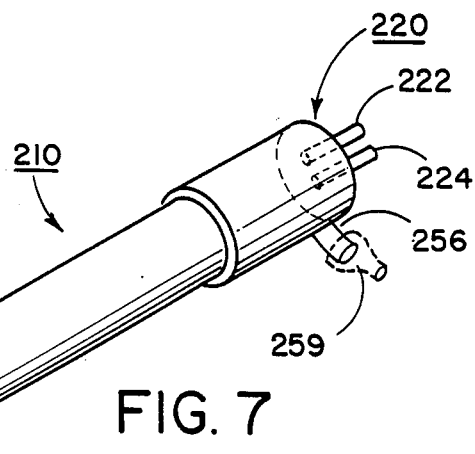
FIG. 7
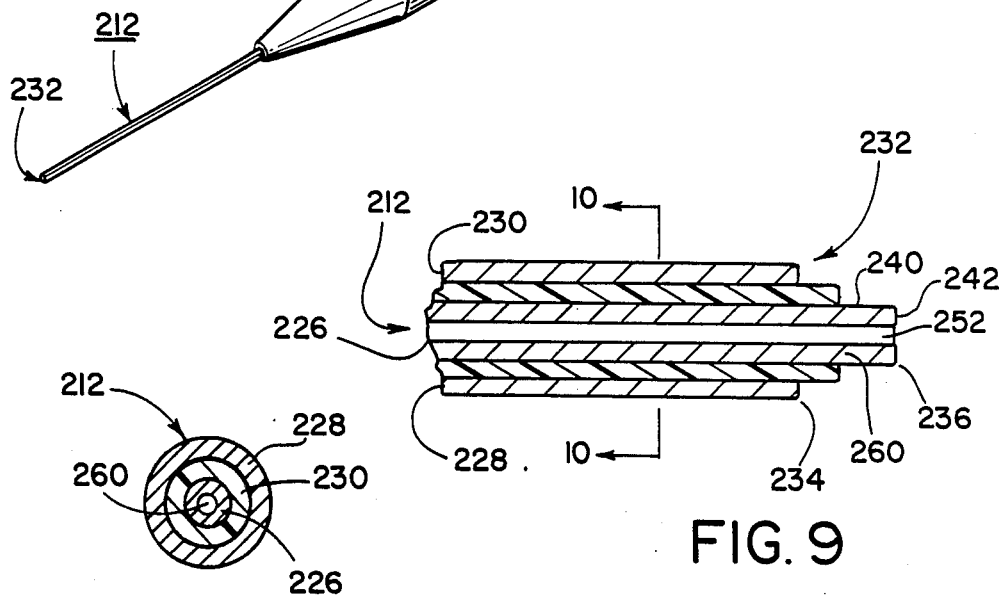
FIG. 9
FIG. 10

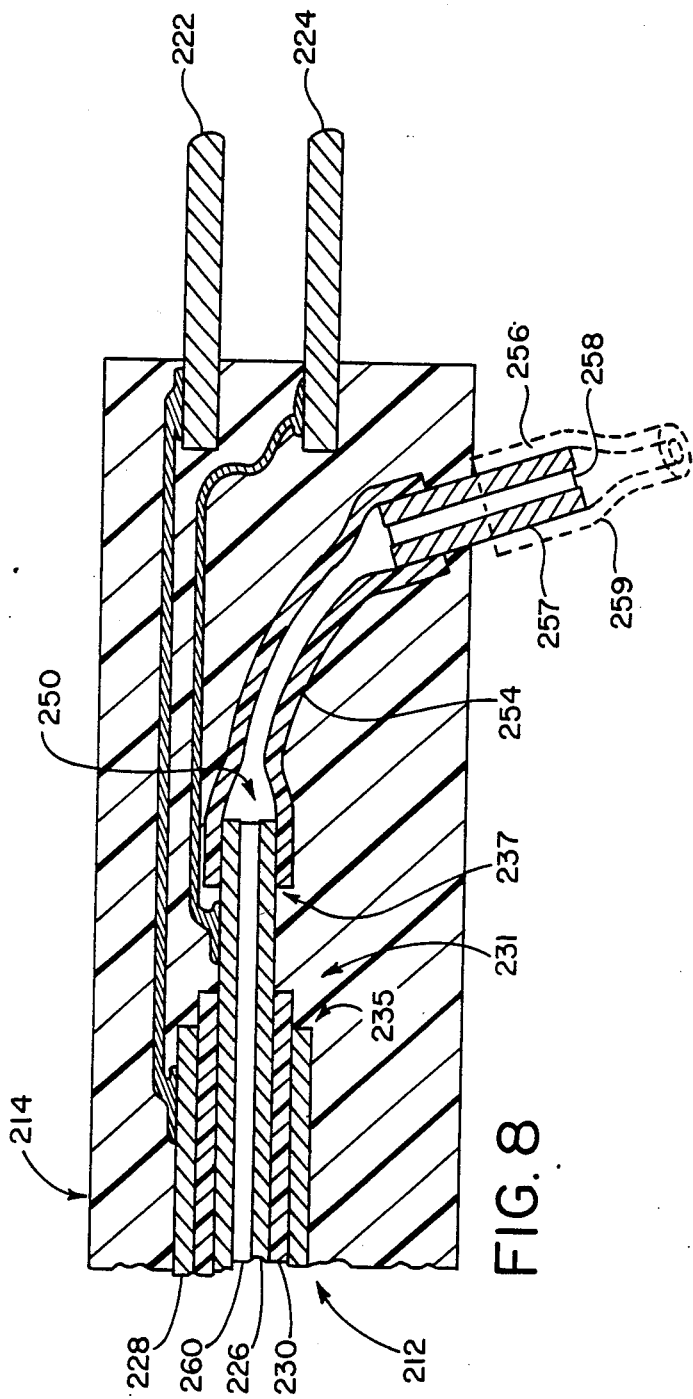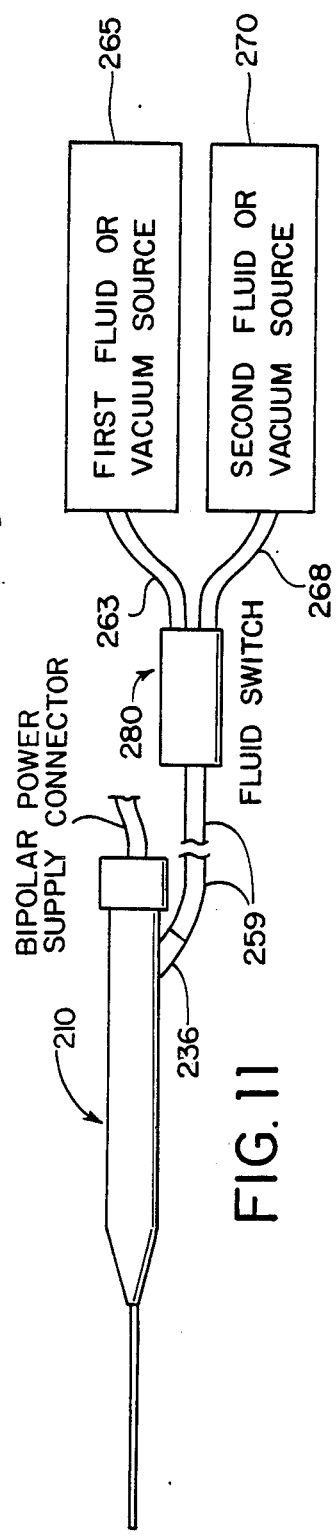

COAXIAL BIPOLAR PROBE

This application is a continuation-in-part of application Serial No. 611,867, filed May 18, 1984 and now abandoned, which was a division of pending application Serial No. 428,849, filed Sept. 30, 1982 and now U.S. Pat. No. 4,476,862, which was a division of Serial No. 213,861, filed Dec. 8, 1980 and now abandoned, which was a continuation of application Ser. No. 900,422, filed Feb. 5, 1979 and now abandoned, all of which are incorporated by reference.

BACKGROUND OF THE INVENTION

This invention relates to electrosurgical devices and in particular to an electric probe for use in performing ophthalmic and other types of electrocautery and electrocoagulation operations. One skilled in the medical arts will appreciate that the coagulation of protein is a precursor to cauterization of tissue. The use of the word cautery hereinafter with respect to the subject invention will be understood to encompass coagulation, where that operation is also appropriate.

Electricity has been used to cauterize tissue in essentially two different ways. One technique comprises the use of an electrical current to heat a resistance element, the heated element then being applied to the tissue to be cauterized. The use of this technique precludes the necessity of applying an electrical current through the tissue. The other technique comprises the application of an alternating current through the tissue which causes cauterization in the vicinity of the electrode tip due to the high current density in this region.

Heretofore, the application of alternating current through the tissue was usually performed by using either a unipolar or bipolar technique. In the unipolar technique, the patient is placed on a ground plate which forms one electrode. The other electrode comprises a probe disposed in an insulated handpiece. The ground plate and the probe are electrically connected across the terminals of a high frequency voltage source. Using this technique, the tip of the probe is applied to the tissue. The current flows between the probe and the ground plate, with cauterization occurring in the vicinity of the probe tip due to the high current density in this region. This technique has several disadvantages, among which are the possibility of ground plate burn. In addition, this technique requires that the tissue area be relatively dry and uniform in order to obtain repeatable results without having to constantly adjust the output of the high frequency power supply.

Another technique involves the use of bipolar forceps as an electrosurgical instrument. The destructive effects of this instrument are passed between two points in the field, each blade of the forceps constituting one electrode. This instrument can be used in a wet field, and, since current passes from one blade to the other, only that tissue grasped in the forceps will be coagulated and the spread of coagulation to adjacent tissue is prevented. Bipolar forceps have been used for electrocautery in tonsillectomies (See article entitled "Bipolar Forceps for Electrocautery in Tonsillectomy", Reed, et al, Transactions of AAOO, Vol. 78, 1974) and has also been used in ophthalmic applications (See "Bipolar Coagulation in Ophthalmic Operations", McPherson, Jr., American Journal of Ophthamology, Vol. 73, No. 5, May, 1972). In the bipolar forceps instrument, the distance between the tips are variable in most cases; therefore there is variable coagulation with the same setting of the power supply. There are also forceps in which the distance between the tips is fixed. However, although the coagulation is more uniform when this type of forcep is used, the result is a linear or line coagulation or a smudge. Such linear coagulation or smudge is undesirable in microsurgery or scleral marking.

More recently, probes of bipolar design have been developed. Many of these probes have been designed for coagulation of the vas or other vessels and have coaxial electrodes with exposed tip portions which are axially spaced and have a tapered head for insertion into a vas or other body vessel. Such probes are described, for example, in U.S. Pat. Nos. 1,983,669 to Kimble, 3,920,021 to Hiltebrandt and 4,034,762 to Cosens et al. Such probes are also described in "Vas Cautery Battery-Powered Instrument for Vasectomy," Schmidt et al, UROLOGY, May 1974, Volume III, 5 pages 604–605; and in "An Electrocautery Instrument for the Fulguration of the Vas Deferens During Vasectomy for Sterilization", Decker et al., ISA BM 7330z (5-10), 1973. Still other probes like, the Mentor O&O Wet-Field TM Hemostatic Erase are blunt headed, i.e. there is no axial displacement between the extreme exposed end surfaces of the two electrodes at the tip of the probe so that the two electrodes and insulating spacer therebetween form a common plane at the tip. This allows the probe tip to be "wiped" across a flat, working field in sweeping movements to cauterize the ends of vessels and other tissue exposed on the field. Both of these types of bipolar probes are unsuitable for scleral marking. In that procedure an instrument is pressed against tne outer surface (scleral coat or sclera) to mark locations corresponding to items observed within the eye cavity by the surgeon. The aforesaid bipolar probes are unsuitable for scleral marking and like microsurgical procedures, the geometry and spacing of the electrodes making it difficult if not impossible, to bring both electrodes to bear against the sclera without damaging it or protruding into the sclera in such a manner as to make the location of the axial, marking electrode, difficult, if not impossible, to discern.

SUMMARY OF THE INVENTION

In order to overcome those problems attendant with unipolar and bipolar forceps techniques for electrocautery, applicant's invention discloses a coaxial bipolar probe apparatus for precisely limiting the cautery to a predetermined area in either a wet or dry field. The apparatus comprises an elongate cylindrical axial electrode having a first end which forms a portion of the probe region. A hollow tubular outer electrode, which is electrically insulated from the axial electrode, is coaxially disposed around the axial electrode. The outer and axial electrodes are adapted for electrical connection to high frequency power supply from which a high frequency alternating voltage is applied between the axial and outer electrodes. The outer electrode has a first end which also forms a portion of the probe region of the apparatus. The first end of the axial electrode protrudes slightly beyond the first end of the outer electrode. To make the axial electrode more visible for scleral marking the first end of the preferred axial electrode is blunt with a partially exposed cylindrical side wall. The axial spacing between the extreme protruding ends of the axial and outer electrode is between about 0.6 mm and 1.0 mm and preferably between about 0.7 mm and 0.8 mm. In a preferred embodiment, an axial lumen is also provided through the center of the axial electrode from the probe region tip of the axial electrode. The lumen forms part of a hollow channel to dispense fluids or present a partial vacuum for aspiration at the probe tip. The opposing end of the lumen is fluidically coupled through a tube to a connector adapted for coupling with a partial vacuum source or fluid source or an intermediate switch mechanism so as to provide a vacuum or fluid as desired or both in alternation as selected, through the lumen at the probe tip.

The probe region, with the high frequency voltage applied across the electrodes thereof, is placed in contact with the tissue area to be cauterized. When contact is made, the electrical current flows in a radial direction between the axial electrode and the coaxial outer electrode. The current density is inversely proportional to the square of the distance from the axial electrode to the coaxial outer electrode. Consequently, the area of cauterization will be substantially circular having a diameter which is proportional to the voltage applied between the electrodes. Consequently, the use of this apparatus will provide spot cauterization having a well defined area. In addition, since a bipolar technique is employed, electric current will not flow through the patient's body thereby negating the possibility of concomitant adverse side effects.

The preferred probes provide improved performance over conventional probes in certain diathermy procedures including retinal attachment and scleral marking and, with axial lumen in nucleus removal.

The subject probes with axial lumen coupled to an irrigation source or a vacuum source or both are also extremely useful in other microsurgical procedures such as nasal or otologic cautery procedures where small passages make flushing of the work site and/or aspiration of blood, lymphatic fluid and/or cautery by-products difficult, if not impossible to accomplish simultaneous with cautery.

Accordingly, it is an object of the present invention to provide a novel bipolar electrode probe for electrocautery capable of greater pinpoint accuracy in microsurgery and scleral operations.

It is a further object of this invention to provide an apparatus for producing cautery spots of predetermined areas.

Another object of the present invention is to provide an apparatus which produces spot cauterization without passing a current through a patient's body.

It is a further object of the present invention to provide an apparatus for producing repeatable marks for use in procedures such as scleral marking.

As a further object of the present invention to provide a probe apparatus for improved visibility through the sclera.

It is a further object of the present invention to provide an apparatus for providing fluid or aspiration, as desired, simultaneous with electrocautery.

As a further object of the invention to provide an apparatus for selectively supplying fluid or aspiration simultaneously or sequentially, as selected, with electrocautery.

These and other objects of my invention will become apparent from the following description with reference to the accompanying drawings.

BRIEF DESCRIPTION OF THE DRAWINGS

FIG. 6 is a longitudinally sectioned view of the terminal or probe region of a second, untapered coaxial bipolar probe embodiment of the present invention.

FIG. 7 is an isometric view of a preferred coaxial bipolar probe embodiment of the present invention including an axial lumen through the axial electrode.

FIG. 8 is a longitudinally sectioned view of the FIG. 7 apparatus in the electrical and lumen connection portion of the handpiece.

FIG. 9 is a longitudinally sectioned view of the terminal or probe region of the preferred embodiment bipolar probe with axial lumen.

FIG. 10 is a transverse sectioned view of the terminal or probe region along the lines 10—10 in FIG. 9.

FIG. 11 depicts diagrammatically the coupling of the distal end of the axial lumen with a plurality of fluid and/or vacuum sources through a switching device.

DETAILED DESCRIPTION OF THE INVENTION

Figure 1:
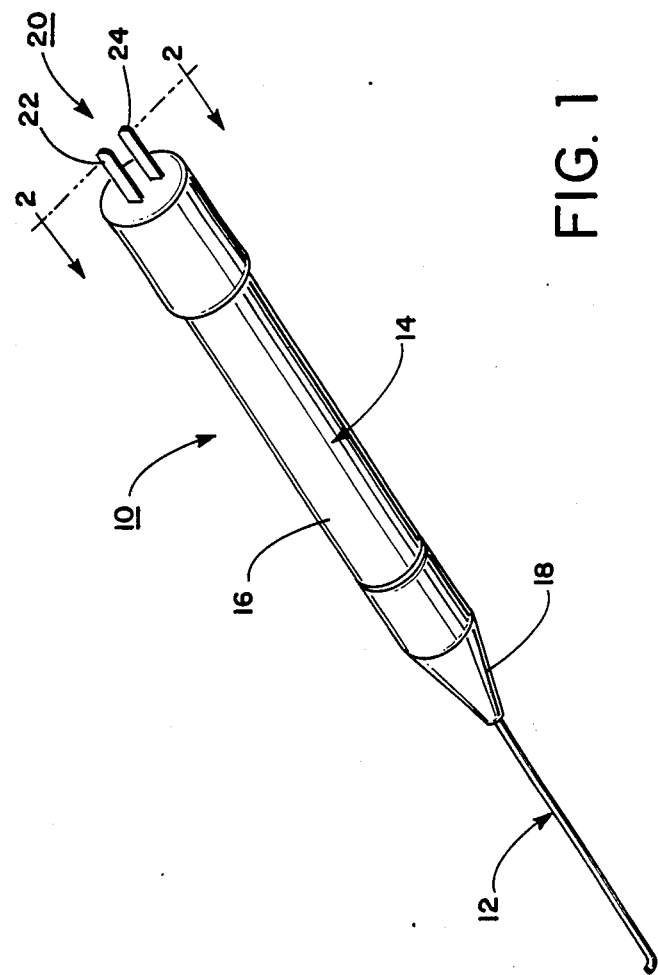
FIG. 1 is an isometric view of a first embodiment of the coaxial bipolar probe of the present invention.

In FIG. 1 there is shown an embodiment of the coaxial bipolar probe of the present invention designated generally 10. The probe 10 includes an electrode portion 12 disposed in a handpiece portion 14. In the preferred embodiment, the handpiece portion 14 is made of an electrically insulating polymeric material, such as teflon (polytetrafluoroethylene) or polysulfone, configured in a pencil-shaped form having a cylindrical body region 16 and a tapered forward region 18. Although a pencil-shaped configuration is preferred, it should be noted that any configuration of the handpiece portion 14 which is easily, comfortably, and conveniently grasped in the hand will also be suitable and is considered within the scope and contemplation of my invention. The end of the handpiece portion 14, remote from the tapered portion 18, includes an electrical connection portion designated generally 20. The electrical connection portion 20, preferably comprises a pair of electrically conductive pins 22 and 24 adapted for mating in a female receptacle (not shown). The female receptacle is in turn electrically connected to the output of a high frequency bipolar power supply, for example, a standard electrosurgical power unit with reduced power and bipolar output, such as is manufactured by Codman and Shurtleff, Inc. or Green-Line Surgical Intstruments. Units distributed by Stortz and by Mentor O&O Inc. are usable but do not appear as effective. When inserted in the female connector, the pins are therefore electrically connected to the output of the high frequency power supply.

Figure 2:
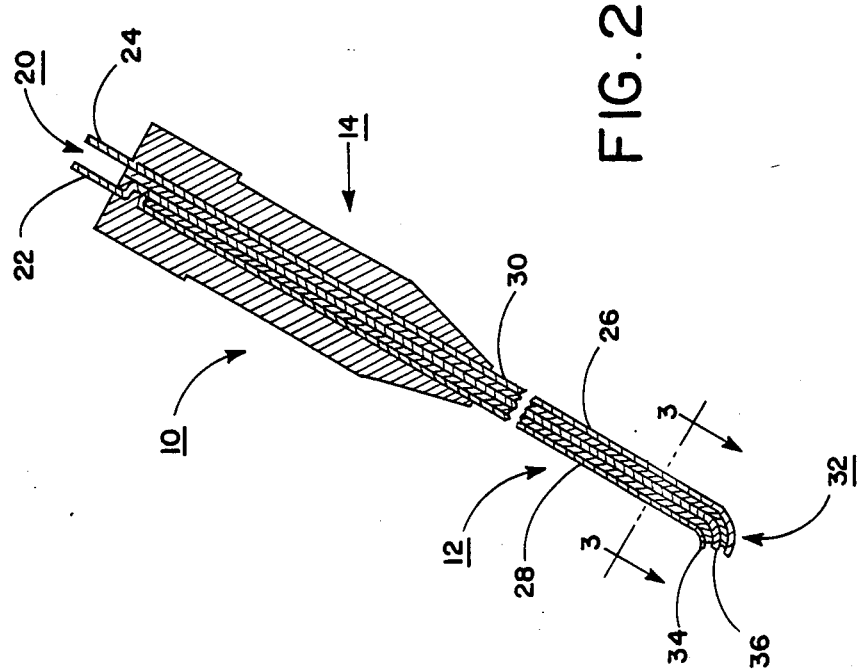
FIG. 2 is a cross section taken along lines 2—2 of FIG. 1.

Referring now to FIG. 2, there is shown a cross section of the embodiment of the coaxial bipolar probe shown in FIG. 1. As shown in FIG. 2, the electrode portion 12 comprises an elongate cylindrical axial or central electrode or conductor 26 and an elongate, hollow tubular outer electrode or conductor 28 which is coaxially disposed around the inner electrode 26. The inner and outer electrodes are made of an electrically conductive material, preferably stainless steel or other corrosive resistant conductor. The coaxial relationship and spacing between the axial and outer electrodes is maintained by inserting an electrically insulating polymeric material 30 therebetween, such as TEFLON (polytetrafluoroethylene) or polysulfone in the preferred embodiment.

Figure 4:
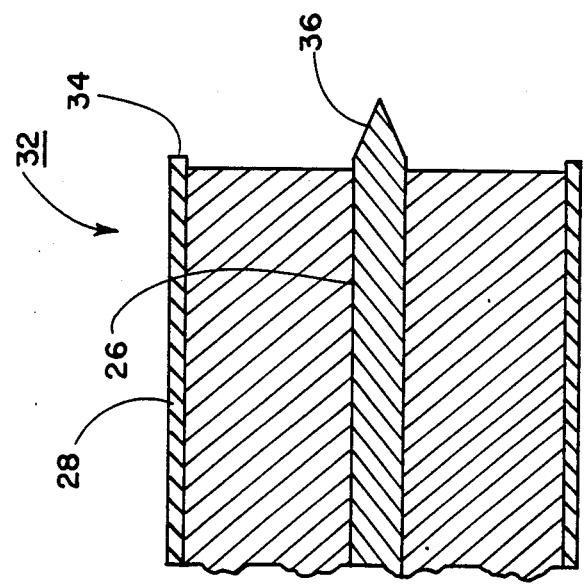
FIG. 4 is a cross section of a terminal or probe region of the first coaxial bipolar probe embodiment of the present invention.

One end of the electrode portion 12 comprises a probe region designated generally 32 (see FIG. 2 shown in greater detail in FIG. 4). As is indicated in FIG. 4, the probe region 32 includes a first end 34 of the outer conductor 28 and a first end 36 of the axial conductor 26. In the depicted embodiment, the first end 36 of the axial conductor 26 protrudes slightly beyond the first end 34 of the outer conductor 28 in order to effectuate good tissue contact. As is shown in FIGS. 2 and 4, the first end 36 of the axial conductor 26 of this embodiment is tapered down to a point. It should be noted that the first end 36 may terminate in a sharp point, a dull point, or have no taper whatsoever depending upon current density characteristics desired. Consequently, all of these first end configurations are considered to be within the scope and contemplation of my invention. I have discovered that an untapered protruding axial electrode in as step-like fashion with the tubular insulation from an outer electrode, particularly in combination with a flat, transverse tip surface as is illustrated in a second embodiment probe tip depicted in FIG. 6, is the best type of tip for scleral marking and other ophthalmic procedures. The blunt tip makes the protruding axial electrode of the probes more visible when viewed from the inside of the eye as the probe is pressed against the outer surface (i.e. sclera) of the eye for marking. The step-like configuration with tiers and blunt tip allows the tip of the probe to be pressed against the various parts of the eye sufficiently for good contact while preventing penetration. A preferred embodiment device including an axial lumen through the axial electrode is depicted in FIGS. 7 through 10 and will, with the embodiment of FIG. 6, be subsequently discussed.

It should be noted that the probe region as shown in FIG. 2, is curved through approximately 90 degrees. This type of curve may be suitable for a specific application such as scleral marking. However, a straight probe may be more suitable for another application and probe regions having curved portions to meet other specific applications are considered to fall within the scope and contemplation of my invention.

Referring again to FIG. 2, the ends of the axial and outer electrodes remote from the probe region 32 are electrically connected to the pins 22 and 24 respectively. Consequently, when the pins are connected to the mating female connector which is in turn electrically connected to the power supply, and the power supply is energized, the high frequency voltage output from the power will appear between the axial electrode 26 and the outer electrode 28.

Figure 3:
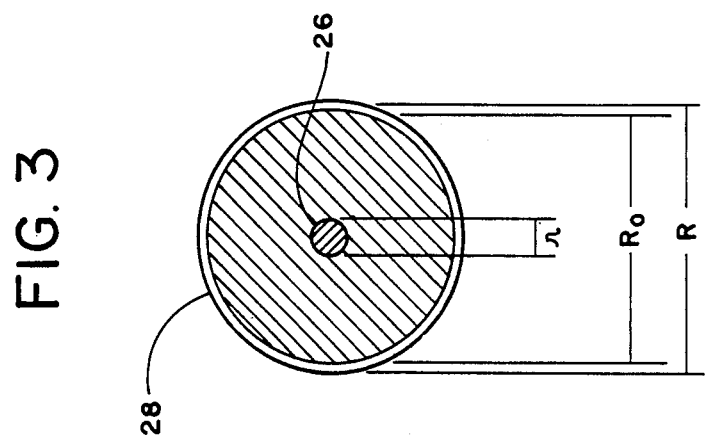
FIG. 3 is a cross section taken along lines 3—3 of FIG. 2.
Figure 5:
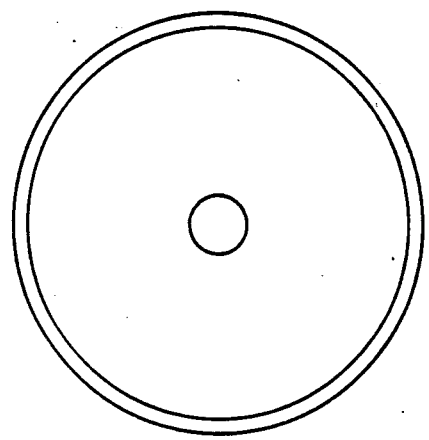
FIG. 5 is an end view of the terminal or probe region shown in FIG. 4.

The preferred dimensions of the electrodes, at least in the probe region 32, are hereinafter discussed in conjunction with FIG. 3. As shown in FIG. 3, the axial electrode 26 has a cross sectional diameter designated r. The inner diameter of the outer electrode 28 is designated $R_O$ and the outer diameter is designated R. The dimensions r, $R_O$ and R have variable sizes depending upon the use of the probe, for example, whether used in general surgery, specialty surgery, or in microsurgery. For use in general and non-microsurgery, the preferred ranges are r = 1.0 mm-10.0 mm; R, $R_O$=2 mm-30 mm; and R-$R_O$ 0.5 mm-1.0 mm. For use in microsurgery, the preferred dimensions are: r=0.1 mm-0.5 mm (note that if required, the tip of the axial electrode 26 of the first embodiment may be tapered to a point having a diameter which is smaller than 0.1 mm); R, $R_O$=0.5 mm-5 mm; and R-$R_O$=0.1 mm-1.0 mm. A preferred prototype embodiment of the apparatus depicted in FIGS. 2-5 for microsurgery applications has the following dimensions: r = 0.3 mm, R = 1.0 mm, and $R_O$= 0.9 mm. A preferred prototype embodiment of the same apparatus for use in general and non-microsurgical applications has the following dimensions: r=1.0 mm, $R_O$=3.0 mm, R=3.5 mm.

FIG. 6 depicts the probe region, designated generally as 132, of the electrode assembly of a second bipolar probe embodiment of the subject invention preferred for use in scleral marking and other opthalmic procedures where there is a danger of unintentionally piercing the eye. The probe region 132 includes a first end 134 of an outer conductor 128 and a first end 136 of an axial conductor 126. As in the embodiment of FIGS. 2-5, the first end of the axial conductor 126 of this embodiment protrudes distinctly beyond the first end 134 of the outer conductor 128 in order to effectuate good tissue contact. The first end 136 of the axial electrode includes an exposed, untapered cylindrical side wall surface 140 terminating in a flat, exposed transverse end surface 142. A radius is provided around the circumference of the intersections of the two surfaces 140 and 142. A tubular layer of electrically insulating material 130 is coaxially disposed between the axial and outer electrodes and is axially exposed in the probe region 132 between the first ends 134 and 136. The distance "1" between the transverse end surface 142 of the axial electrode 126 and the proximal edge 131 of the insulation 130 is at least about 0.2 mm and preferably between about 0.35 and 0.45 mm. The distance L between the transverse end surface 140 of the axial electrode 128 the transverse end surface 135 of the outer electrode 128 is at least about 0.2 mm and preferably between about 0.78 and 0.88 mm. The smaller values of the preferred dimension ranges are for smaller probes. The axial electrode diameter, r, and the outer electrode outer and inner diameters R and $R_O$ are the same as those set forth for the embodiment of FIGS. 2-5 for general surgery and microsurgery applications.

FIGS. 7 through 10 depict in various views, another embodiment of the present invention preferred where the application of irrigation, air or a vacuum is needed in the work field. Referring to FIG. 7 the probe is generally designated as 210 and again includes an electrode assembly portion indicated generally as 212 disposed in a handpiece portion 214. The handpiece portion 214 is made-of an electrically-insulating material such as TEFLON (polytetrafluoroethylene) or polysulfone or similar polymeric material, configured in a pencil-shaped or other form, adapted to be hand held by a user. One end of the electrode portion 212 comprises the probe or terminal region and is designated generally as 232. The probe region is depicted in sectional and end views in FIGS. 9 and 10 and includes a first end 234 of an outer conductor 228 and a first end 236 of an axial conductor 226. Again, a concentric layer of electrically-insulating polymeric material 230 is disposed between the axial electrode 226 and the outer electrode 228. The axial electrode 226 is also provided with a central lumen 260 along its entire length and terminating in an opening 252 through the transverse end surface 242 of the electrode 226 at the probe end 232 of the assembly 212. Referring again to FIG. 7, the end of the handpiece portion 214 opposite from the protruding electrode probe region 232, includes an electrical connection portion designated generally as 220, which is the same as the electrical connection portion 20 of the embodiment of FIGS. 1 and 2. The electrical connection portion 220 preferably comprises a pair of electrically conductive pins 222 and 224 adapted for mating with a female power receptacle (not shown). The female receptacle is, in turn, electrically connected to the output of a high frequency bipolar power supply (not depicted) such as is conventionally used with existing bipolar coagulators. The device 210 is provided with a hollow channel extending from the extreme tip of the probe region 232 of the axial electrode assembly 212 through the assembly to its opposite end within the handle 214 from which it continues to a fluid connector 256 protruding from the handle. The lumen 260 provides the portion of the channel 250 extending through the electrode assembly 212. As is depicted in FIG. 8, a hollow tubing 254 sealingly connects the handle end 237 of the axial electrode allowed to extend beyond the opposing end 235 of the outer electrode 228 where the handle end 231 of the electrode assembly 212 terminates within the handpiece 214, to the fluid connector 256 externally mounted on the handpiece 214. The channel 250 terminates in an opening 258 at the tip of the connector 256. The outer surface 257 of the connector may be cylindrical as depicted or configured so as to more sealingly engage and hold a piece of elastic flexible tubing 254 or the like, as indicated in phantom. Alternatively, the tube 259 can be coupled with a connector 256 by conventional means (not depicted). Also, the extreme end 237 of the axial electrode 226 can be passed through the handle 214 on place of the connector 256 and tube 259, although the depicted arrangement is preferred. The channel 250 can be used to introduce an irrigating fluid, compressed air or a partial vacuum at the tip 232 of the assembly. Coaxial positioning of the channel 250 at the tip 232 is important in that an electrolytic irrigating fluid such as saline can be introduced through the tip without severely distorting the current flow characteristics of the tip. Furthermore, the provision of the lumen at the end of the protruding tip allows pinpoint application of fluid or a partial vacuum and, being centrally positioned, makes it easier for the user to estimate the location of the channel even though unable to see it when using the instrument.

If desired, a fluid switch, indicated diagrammatically as a box 280 in FIG. 11, may be connected between the connector 256 and lines 263 and 268 from several fluidic and/or vacuum sources, only two of which are diagrammatically indicated as boxes 265 and 270 for clarity. The switch 280 fluidically couples the connector 256 to any one of the two (or more) sources 265 and 270 or seals the end of the connector 256 (and probe channel 250) from all fluid and/or vacuum sources, as desired. The details of the switch 280 provide no part of the subject invention and it is assumed that it may be provided in a variety of arrangements including arrangements where the surgeon may operate the switch by means of finger controls in the handgrip of the instrument 210. Also a number of vacuum and/or fluid sources with individual controls can be fluidically coupled with the connector 256 by replacing the switch 280 of FIG. 11 with a multi-branch fluid connector and providing individual on-off controls, such as conventional pedal operated solinoid pinch valves, in the source feed lines 263 and 268, or in the sources themselves. All such switches and controls used in connection with an axial lumen in a bipolar coaxial probe are intended to be encompassed by the subject invention. A conventional, electrically powered surgical vacuum source or even an aspiration bulb can be used with the probe of the present invention for ophthalmic procedures such as denatured nucleus aspiration and nucleus removal, as will be subsequently described. It has further been found that the coupling of an elevated irrigation source such as a bag or bottle of saline solution to the connector tube 256 of the probe apparatus 210 provides a controllable gravity fed irrigation system suitable for most electrocautery applications.

Figure 12:
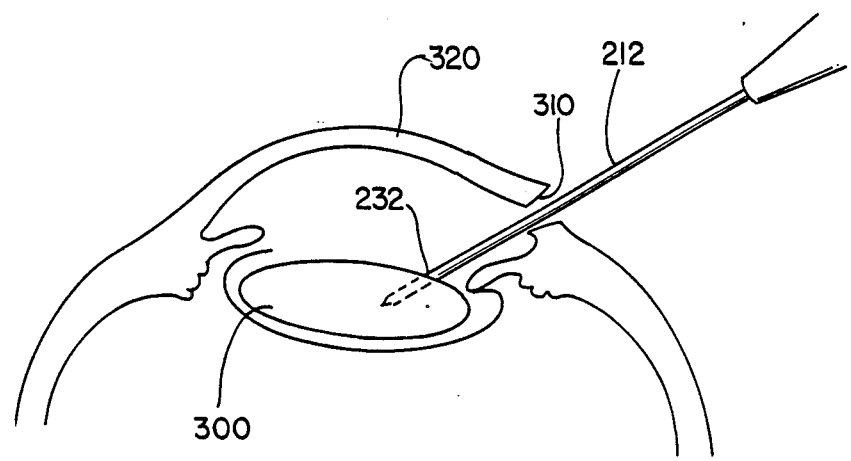
FIG. 12 depicts the denaturement and breakup of a lens nucleus in vivo using a coaxial bipolar probe.
Figure 13:
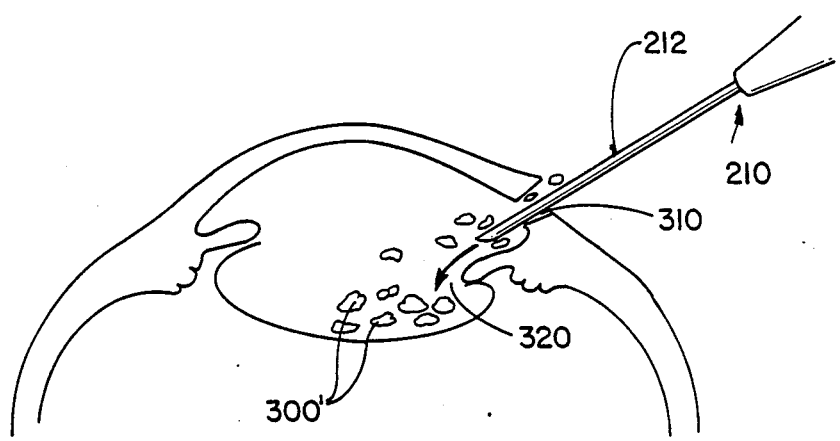
FIG. 13 depicts diagrammatically the flushing of a denatured nucleus from the eye by the introduction of irrigation through the axial lumen of the preferred embodiment probe.

The diameter r of the axial electrode 126 and inner and outer diameters $R_O$ and R, respectively, of the outer electrode 128 of the embodiment of FIG. 6 is the same as those previously given for the embodiment of FIGS. 1 through 5. The dimensions of the probe electrode assembly must be sufficiently large to accommodate the lumen. The diameter of the axial lumen is less than the diameter of the axial electrode, yet sufficiently large to allow a sufficient fluid flow. One embodiment having an outer electrode corresponding in diameter to a standard 15 gauge hypodermic needle, an axial electrode diameter of about 0.8 mm and a lumen diameter of about 0.5 mm has been successfully tested The preferred probe with axial lumen is envisioned to be employed for the phacocoagulysis of a cataractous nucleus. The device can be used in a variety of ways as is depicted in the subsequent figures. The probe 212 is inserted through a small limbal incision opening 310 in the cornea is placed in firm contact with the nucleus 300 as shown in FIG. 12 and the bipolar power supply activated (any suggestions on current level). Heat generated by current flow between the electrodes at the probe tip 232 softens (i.e., denatures) the nucleus allowing the tip to penetrate, indicated in phantom, liquifing tissue in its path. The nucleus may be fragmented into large pieces by piercing it a number of times in this manner. The large pieces 300 can be expressed through a small incision by the introduction through the lumen of irrigation, as is indicated diagrammatically in FIG.

Figure 14:
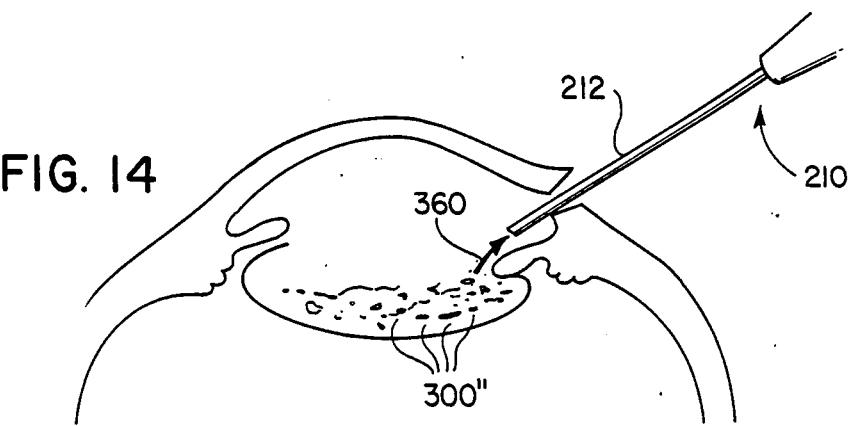
FIG. 14 depicts diagrammatically the aspiration of the broken up nucleus through the axial lumen of the preferred embodiment probe.

13, or other source aspirated using a larger lumen (not depicted). If desired, the nucleus fragments may also be further broken up and/or dissolved with the probe into liquid and pieces 300″ sufficiently small to be aspirated through the lumen 260 of the probe 210, as is indicated diagrammatically in FIG. 14 by the arrow 360.

Figure 15:
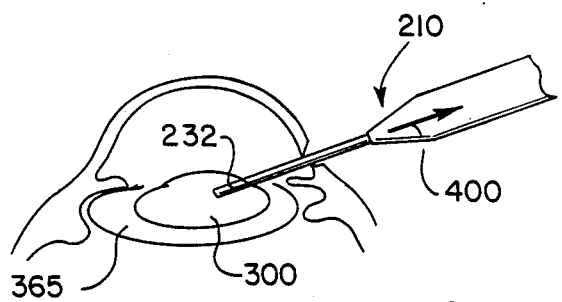
FIG. 15 depicts diagrammatically the attachment of the terminal region of the preferred embodiment probe with lumen to a lens nucleus.
Figure 16:
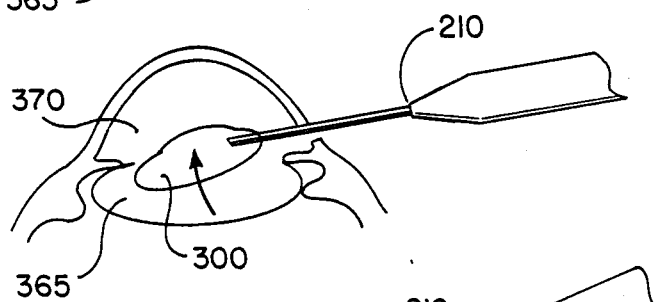
FIG. 16 depicts diagrammatically the movement of the affixed nucleus of FIG. 5 into the anterior chamber with a lollipop maneuver.
Figure 17:
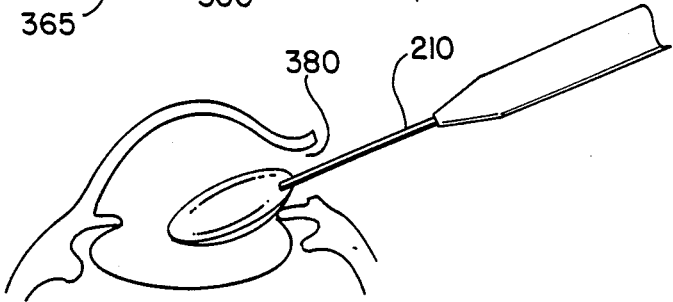
FIGS. 17 depicts diagrammatically the removal of the affixed nucleus of FIGS. 15 and 16 from the anterior chamber through a large corneal incision.

Any of the aforesaid methods allow the removal of the nucleus through a small limbal incision. Alternatively, the nucleus may be removed intact using the preferred device 210. The nucleus is connected by the probe tip 232 as is depicted diagrammatically in FIG. 15, and a partial vacuum is created within the lumen as indicated by arrow 400 fixing the nucleus to the probe tip. Activating the probe power supply briefly will coagulate the surface of the nucleus forming a seal about the electrode assembly tip maintaining the vacuum. As is depicted diagrammatically FIG. 16, the nucleus can then be manipulated from the posterior chamber the anterior chamber 310 and as indicated in FIG. 17 removed from the eye through the opening 380 of a large corneal incision using a "lollipop" technique. All of these techniques eliminate or minimize the need to apply counterpressure at the "6 o'clock" position and minimize or eliminate the need for superior scleral depression at the "12 o'clock" position, further reducing trauma to the eye.

The preferred probe with axial lumen can also be used to aspirate residual cortical material after the removal of the lens nucleus during an extracapsular cataract extraction.

The bipolar probes of the subject invention have also been successfully employed for diathermy application to a scleral bed in reattaching a detached retina. Unipolar probes heretofore used in this procedure performed inconsistently providing "welds" of nonuniform size and of various binding effect.

The preferred embodiment device with axial lumen has also been found a superior coagulation device for use in nasal passages, ear canals and other areas where dimensional restrictions limit the number of instruments which can be applied to the work field at any given time. As a coagulator, the preferred bipolar probe with axial lumen allows the aspiration of blood and coagulation by-products from the work field or, if desired, the introduction of irrigation to wash away blood and other fluid and coagulation by-products simultaneous with cautery.

The coaxial bipolar probes of the present invention are used generally as follows. A conventional medical high frequency bipolar power supply like one of the aforesaid is electrically connected to the axial electrode and outer electrode of the coaxial bipolar probe by means of a female connector mated to the connector pins in the probe device handle. The power supply is energized causing a high frequency alternating voltage output to appear between the axial and outer electrodes. Note, this energization can occur before and after the probe contacts the tissue as desired. The end of the probe region is placed against the tissue causing the first ends of the axial and outer electrodes respectively to come into contact with the tissue. Electrical current then flows through the tissue between the axial and outer electrodes.

The current density is greatest at the tip of the axial electrode and decreases in proportion to the square of the radius in the radial direction toward the outer electrode. This is shown schematically in FIG. 18a where the arrows 38 extend radially from the axial conductor 26 toward the coaxial outer conductor 28. As previously stated, the current density is highest in the vicinity of the axial conductor 26 and decreases in proportion to the square of the radial distance from the axial conductor 26 toward the outer conductor 28. This is also true for the preferred probe with axial lumen.

Figure 18B:
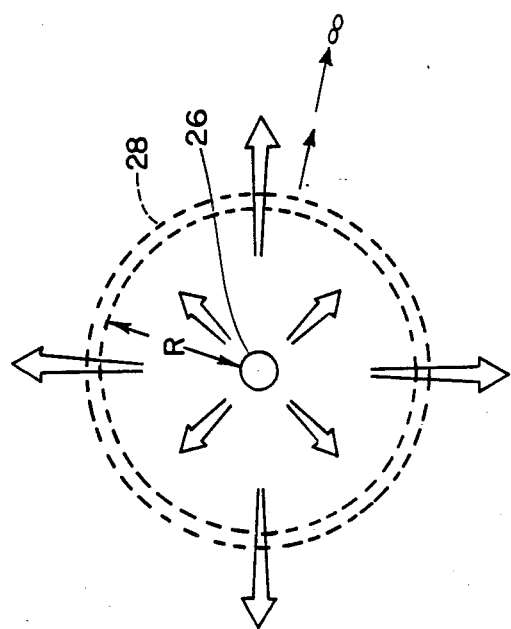
FIGS. 18a and 18b are schematic representations of current density obtained in a coaxial bipolar probe, FIG. 18a showing the case where the outer coaxial conductor is displaced a finite distance from the axial conductor and FIG. 18b showing the special case where the distance between the coaxial outer conductor and the axial inner conductor is infinite.
Figure 18A:
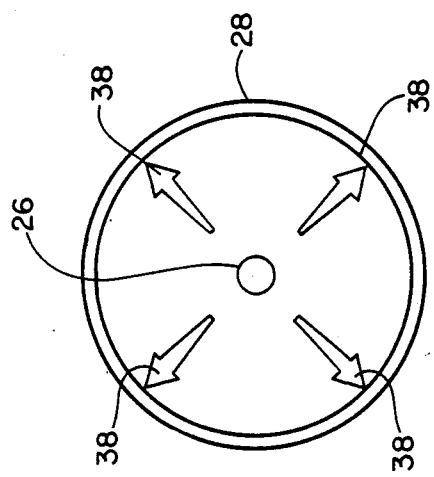

FIG. 18b depicts the special case where the coaxial outer conductor 28 is displaced from the axial inner conductor 26 by a radial distance equal to infinity. This special case approximates that of the unipolar probe wherein the unipolar probe would correspond to the axial conductor 26 and the ground plate corresponds to the outer conductor 28 located at a radial distance which is infinite from the axial conductor 26. In FIG. 18b, the outer conductor 28 is represented by dotted lines to indicate that it is located at a very great distance (approximating infinity) from the axial conductor 26. In the case illustrated in FIG. 18b, the current density is still highest in the vicinity of the axial conductor, or unipolar probe 26, and decreases in proportion to the square of the radial distance away from the axial conductor 26. Note that in this special case, the area of cautery will still approximate a spot since the current density will decrease in substantially radially symmetrical fashion to a point where tissue coagulation or cauterization will no longer occur.

As previously stated, this uniform or radially symmetric decrease in current density could be assumed only when working in a substantially dry field. Even then because resistance between the two electrodes in the latter (FIG. 18b) case will vary so greatly from point to point on the patient and in different directions at any given point, the effect of the unipolar probe will be, in general, neither as predictable nor as uniform as that of the bipolar probe of the subject invention. When using a coaxial bipolar probe of the present invention, wherein the coaxial outer conductor is at a finite radial distance from the axial conductor, the uniformity or spot cauterization effect is enhanced. Consequently, coaxial bipolar probes in accordance with the present invention can be introduced to provide precise spot coagulation. In addition, the configuration of the probes of the present invention enables the achievement of spot coagulation without a charring effect since relatively low power, preferably in the range of 1-15 watts is used. Note, however, that if a charring effect under control is desired, as for example in tissue marking such as scleral marking, an increase in the power applied produces good repeatable marks. In addition, spot accuracy, such as provided by the probe of the present invention, allows the probe to coagulate in areas without shrinking the tissue. For example, it was found that one can control the heating effect so well that it was possible to coagulate small vessels in the limbus region of the eye without shrinking tissue in that area as occurs when using bipolar forceps.

It will be understood that various changes in the details, materials and arrangement of parts which have been herein described and illustrated in order to explain the nature of this invention may be made by those skilled in the art within the principle and scope of the invention as expressed in the following claims.

What is claimed is:

1. An apparatus for cauterizing tissue comprising:
 (a) an elongate insulating body having a first end, an opposing second end, and a bore therein;
 (b) a first elongate electrode having a probe portion and a power supply portion disposed at opposite ends thereof, said probe portion extending beyond the first end of the body and the extreme probe portion end terminating in a substantially planar, transverse end surface;

(c) a second elongate, generally tubular electorde having a probe portion and power supply portion disposed at opposite ends thereof, said tubular electrode extending through said bore with said probe portion extending beyond said first end of the body, said tubular electrode further being coaxial with and spaced radially outwardly from said first elongate electrode, and said tubular electrode having a substantially planar, annular transverse end surface exposed at the extreme probe portion end thereof from which extends the extreme end of said first electrode probe portion with the first electrode end surface in a step tiered relationship with the second electrode end surface;

(d) an insulating tubular sleeve positioned between said first elongate electrode and said second elongate tubular electrode and extending from said probe portion ends of the two electrodes along the length of said coaxial orientation of the two electrodes, a first end of the sleeve terminating in a substantially planar, transverse end surface positioned between the extreme probe portion ends of the two electrodes in a tiered relationship with the extreme probe portion end surfaces of the first and second electrodes; and (e) a pair of power supply connection means each extending from said insulating body and separately connected to a different one of said first and second electrodes near said power supply portion end of each electrode.

2. The apparatus of claim 1 further comprising:
an axial lumen extending from an opening in said transverse end surface of the first elongate electrode coaxially through said electrode to an opening at an opposing end of the electrode.

3. The apparatus of claim 2 further comprising
a hollow elongated connector mounted on an outer surface of said elongate insulating body; and
means for fluidically coupling said connector and said lumen at said power supply portion end of the first electrode within said insulating body.

4. The apparatus of claim 3 in a combination further comprising:
a source of irrigating fluid; and
means for fluidically coupling said source of fluid with said axial lumen through said connector.

5. The combination of claim 4 wherein said source of irrigating fluid is positioned above said probe portion end of the apparatus for gravity feeding through said axial lumen.

6. The apparatus of claim 3 in a combination further comprising:
means for generating a partial vacuum; and
means for fluidically coupling the vacuum generation means with said axial lumen through said connector.

7. The combination of claim 6 wherein said means for fluidically coupling the axial lumen and the vacuum generation means includes a switch for connecting and disconnecting the vacuum from said lumen.

8. The combination of claim 7 further including:
a source of irrigation fluid coupled to said connector through said switch; and wherein said switch is operable to selectively connect and disconnect said lumen with a selected one of the irrigation source and the vacuum generation means.

9. The apparatus of claim 1 wherein said substantially planar transverse end surface of said sleeve is axially spaced between about 0.2 mm and 0.45 mm from said extreme end of said first elongate electrode.

10. The apparatus of claim 9 wherein said substantially planar transverse end surface of said first electrode is also axially spaced between about 0.2 mm and 0.7 mm from said substantially planar transverse end surface of said second electrode.

11. The apparatus of claim 9 wherein said axial spacing between said substantially planar transverse end surface of the sleeve and said substantially planar transverse end surface of said first electrode is between about 0.35 and 0.45 mm and the axial spacing between said substantially planar transverse end surface of said first electrode and said substantially planar transverse end surface of said second electrode is between about 0.7 and 0.8 mm.

12. A hand-held, medical bipolar electric probe apparatus comprising:
an elongated electrode assembly having a pair of elongated electrodes electrically isolated from one another and a first end at which planar, transverse end surfaces of said pair of electrodes are exposed in a step tiered relation;
handle means receiving a second, opposite end of said electrdoe assembly for allowing the assembly to be hand-held by a user;
a pair of electrical connectors exposed on said handle means;
electrical connection means within said handle means for electrically coupling a different one of said pair of electrodes with a separate one of said pair of connectors;
channel means extending from one opening at said first end of the elongated electrode assembly along said assembly and through said handle means to a second opening in a connector means exposed on said handle means and fluidically coupled with said electrode assembly for introducing a selected one of a fluid and a partial vacuum from said connector means through said channel means to said first end of the electrode assembly; and
at least one of the pair of electrodes being electrically insulated from fluid passing along the assembly through the channel means.

13. The apparatus of claim 12 wherein said pair of electrodes are an inner electrode and an outer electrode coaxial at said first end of said elongated electrode assembly and said channel means is formed by a lumen through said inner electrode.

14. The apparatus of claim 13 wherein said two electrodes and said lumen are concentrically cylindrical and coaxial with one another at said tip.

15. An electric medical bipolar probe apparatus comprising:
an elongated electrode assembly having inner and outer coaxial elongated electrodes electrically isolated from one another and a tip at which planar, transverse end surfaces of the two electrodes are exposed in a step tiered relation;
a handle receiving an end of said electrode assembly opposite said tip;
a pair of exposed electrical connectors mounted to said handle;

electrical connection means within said handle for electrically coupling a different one of said pair of electrodes with a separate one of said pair of connectors;

a lumen extending through said inner electrode from an opening at said tip of electrode assembly to an opening at an opposing end of the assembly in said handle; and a hollow, connector extending from said handle and fluidically coupled to the lumen at said opposing end of the assembly for introducing a selected one of a fluid or partial vacuum through the lumen to the tip of the assembly.

16. The apparatus of claim 15 wherein said lumen and said inner and outer electrodes are concentric with one another at said tip.

* * * * *